(12) United States Patent  (10) Patent No.: US 8,915,848 B1
Rixen  (45) Date of Patent: Dec. 23, 2014

(54) APPARATUS AND METHOD FOR EYELID EVERTER

(76) Inventor: James P. Rixen, Waukon, IA (US)

( * ) Notice: Subject to any disclaimer, the term of this patent is extended or adjusted under 35 U.S.C. 154(b) by 0 days.

(21) Appl. No.: 13/560,993

(22) Filed: Jul. 28, 2012

Related U.S. Application Data

(60) Provisional application No. 61/514,028, filed on Aug. 2, 2011.

(51) Int. Cl.
A61B 1/32 (2006.01)

(52) U.S. Cl.
USPC .......................................... 600/235; 600/236

(58) Field of Classification Search
USPC .................................... 600/226, 236
See application file for complete search history.

(56) References Cited

U.S. PATENT DOCUMENTS

| | | | | |
|---|---|---|---|---|
| 1,230,873 | A * | 6/1917 | Crossley | 600/228 |
| 1,400,616 | A * | 12/1921 | McCrory et al. | 600/217 |
| 4,432,347 | A | 2/1984 | Clavin | |
| 4,453,546 | A | 6/1984 | Katz et al. | |
| 4,653,483 | A | 3/1987 | Clavin | |
| 4,694,826 | A * | 9/1987 | Chester | 606/108 |
| 4,883,454 | A | 11/1989 | Hamburg | |
| 5,299,563 | A * | 4/1994 | Seton | 600/215 |
| 5,514,076 | A * | 5/1996 | Ley | 600/206 |
| 5,624,446 | A * | 4/1997 | Harryman, II | 606/96 |
| 5,964,699 | A * | 10/1999 | Rullo et al. | 600/228 |
| 5,971,920 | A * | 10/1999 | Nagel | 600/206 |
| 6,083,153 | A * | 7/2000 | Rullo et al. | 600/217 |
| 6,299,617 | B1 * | 10/2001 | Stamler | 606/107 |
| 6,346,078 | B1 * | 2/2002 | Ellman et al. | 600/235 |
| 6,354,994 | B1 * | 3/2002 | Rullo et al. | 600/217 |
| 6,447,528 | B2 * | 9/2002 | Paraschac | 606/190 |
| 6,811,553 | B2 * | 11/2004 | Anthone | 606/107 |
| 6,979,328 | B2 * | 12/2005 | Baerveldt et al. | 606/41 |
| 7,326,220 | B1 | 2/2008 | Goldstein | |
| 8,197,405 | B2 * | 6/2012 | Lindsay et al. | 600/235 |
| 2005/0159775 | A1 | 7/2005 | Reynolds | |
| 2006/0106370 | A1 * | 5/2006 | Baerveldt et al. | 606/4 |
| 2008/0081952 | A1 | 4/2008 | Josephberg | |
| 2012/0149990 | A1 * | 6/2012 | Buehler et al. | 600/210 |

FOREIGN PATENT DOCUMENTS

| | | |
|---|---|---|
| WO | WO 9520373 A1 | 8/1995 |
| WO | WO 2009096258 A1 | 8/2009 |

* cited by examiner

*Primary Examiner* — Pedro Philogene
*Assistant Examiner* — Lynnsy Summitt

(57) ABSTRACT

An ophthalmic instrument that includes an elongated handle member and a plurality of extensions configured to grasp an eyelid, wherein the extensions extend from a top surface of the handle member at an angle that is substantially perpendicular to a longitudinal axis of the handle member, wherein a first extension is located on a first side of the top surface of the handle member and a second extension is located on a second side of the top surface of the handle member. A double-everting method that includes holding an eyelid to a second end of the handle member and rotating the instrument until the eyelid is placed in an everted position, positioning the plurality of extensions over a lower edge of the everted eyelid in order to grasp the everted eyelid with the plurality of extensions, and rotating the instrument until the grasped-everted eyelid is placed in a double-everted position.

20 Claims, 14 Drawing Sheets

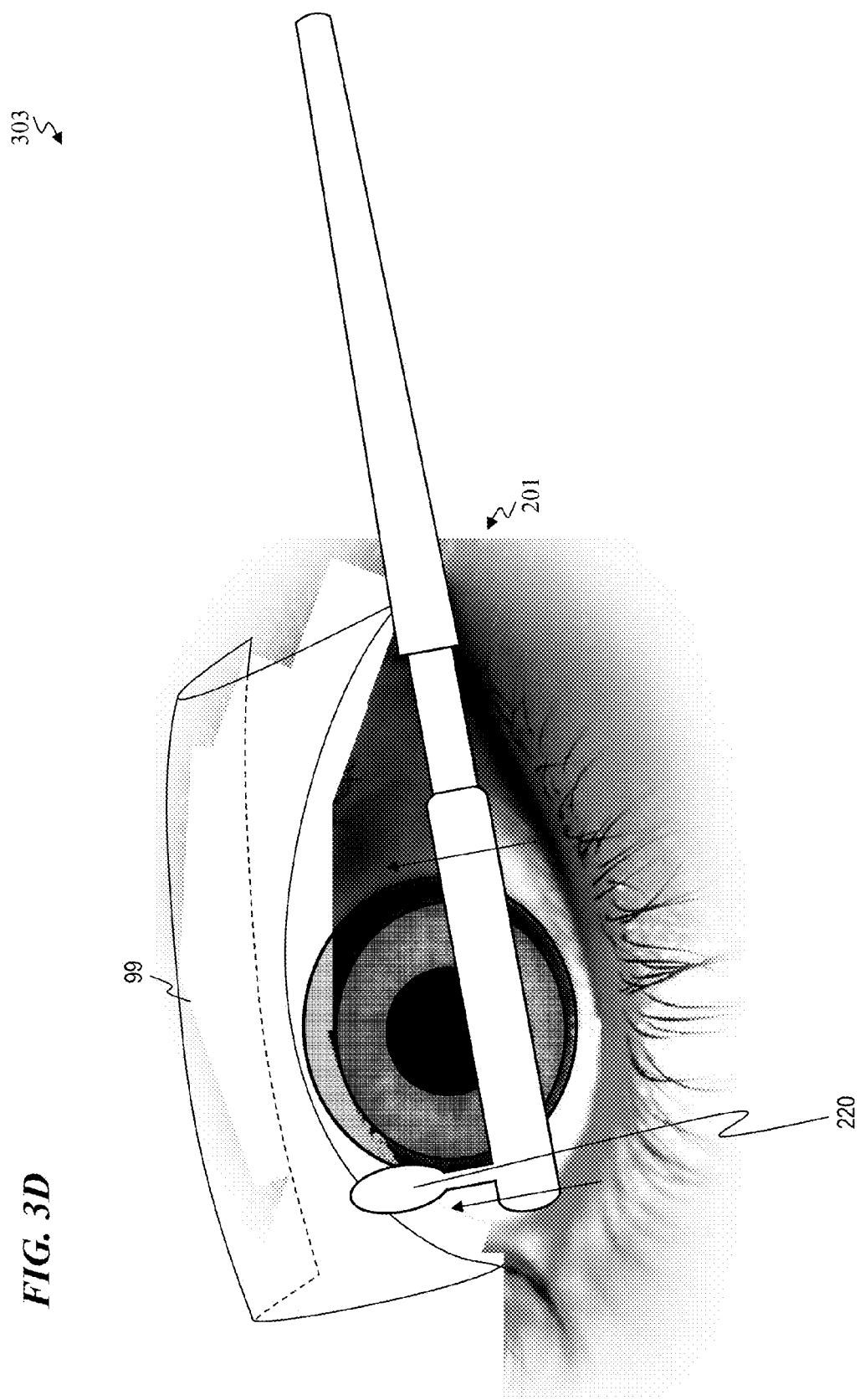

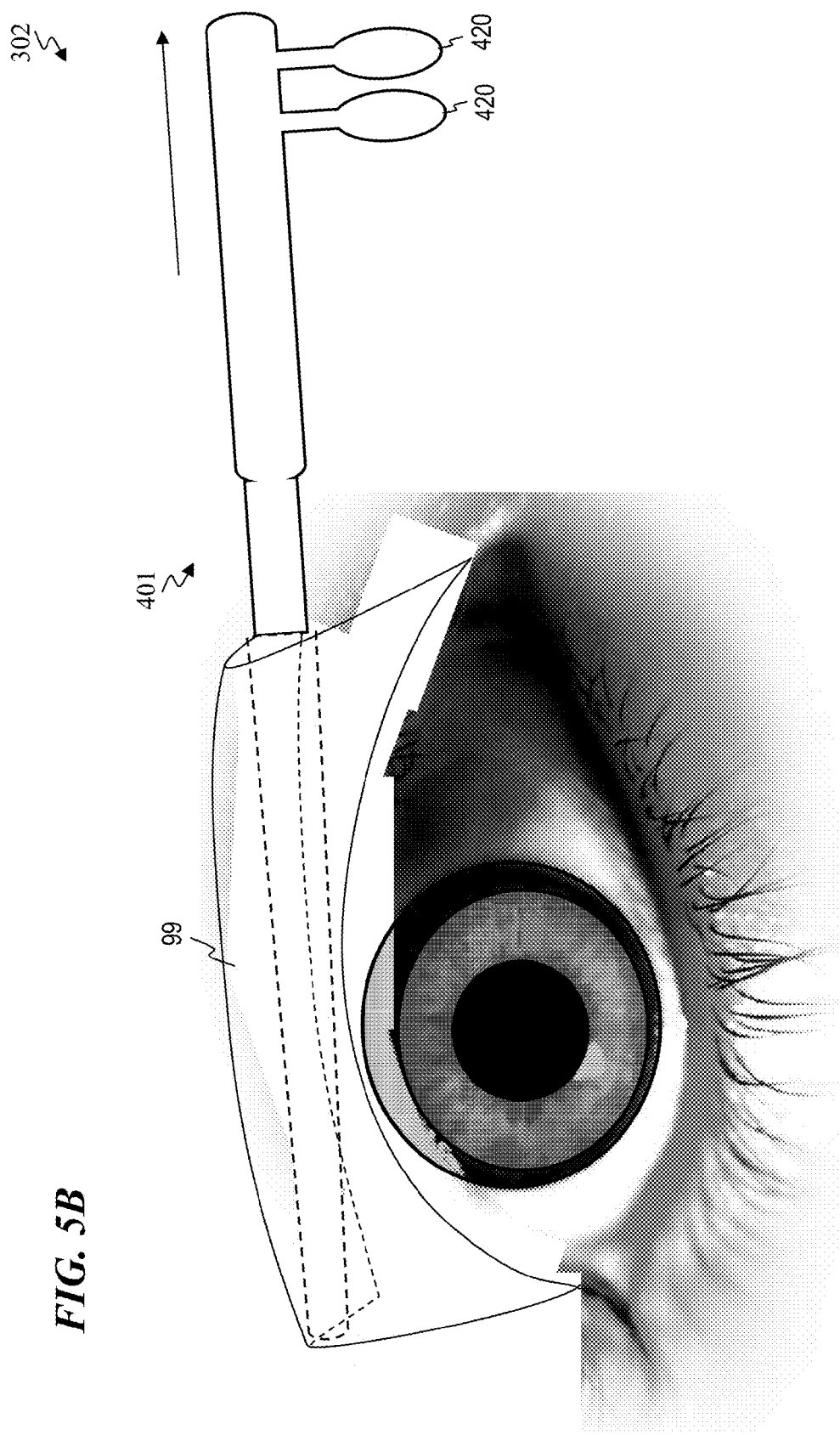

APPARATUS AND METHOD FOR EYELID EVERTER

CROSS-REFERENCE TO RELATED APPLICATIONS

This application claims priority benefit, under 35 U.S.C. §119(e), of U.S. Provisional Patent Application No. 61/514,028 filed Aug. 2, 2011 by James P. Rixen, titled "Apparatus And Method For Eyelid Everter", which is incorporated herein by reference in its entirety.

FIELD OF THE INVENTION

The invention relates generally to ophthalmic instruments, and more specifically to an ophthalmic instrument for everting and double-everting an eyelid.

BACKGROUND OF THE INVENTION

Foreign bodies and even contact lenses are often lodged under the upper eyelid or in the conjunctival fornix of the upper eyelid. A common procedure conducted by eye-care professionals to remove a foreign body lodged in the upper eyelid is an upper eyelid eversion. An eyelid eversion is the turning of an eyelid inside out so as to expose the palpebral conjunctiva. An upper eyelid eversion is accomplished by grasping the lid by the central eyelashes, pulling it downward and forward and then folding it back over a cotton applicator (or thin plastic rod) placed at the upper margin of the tarsus, while the patient continually maintains downward fixation. With the upper eyelid everted, the eye-care professional can more easily access and remove the foreign body. The eyelid is returned to the normal lid position by asking the patient to look up and gently pushing the eyelashes in an outward and downward direction. Eversion of the lower eyelid is performed by drawing the margin of the tarsus downward while the patient looks upward.

Occasionally a foreign body is lodged so far up in the upper eyelid that an eversion of the upper eyelid is not sufficient to see and/or remove the foreign body. In such situations, a double eyelid eversion is required. A double eyelid eversion is an eyelid eversion followed by the turning of the tarsus skin surface of the eyelid inside out such that the fornix skin surface of the eyelid is exposed (in order to make the patient more comfortable, a double eversion is sometimes accompanied by local anesthesia of the conjunctiva). A double eyelid eversion is often carried out using a medical instrument called a Desmarres refractor (a Desmarres retractor is an elongated handheld medical instrument that has a smoothly curved or saddle-shaped spoon-like hook member at one end; see FIG. 1). With the eyelid everted, the hook member of a Desmarres retractor is placed between the two skin surfaces of the eyelid such that the retractor engages the tarsus, and then the tarsus is gently pulled outward and upward until the fornix becomes visible.

Since the longitudinal dimension of a Desmarres retractor generally comes out from the patient's eye toward the eye-care professional during use, it can be extremely difficult to use a Desmarres retractor (to perform, for example, a double eyelid eversion) while also using a bio-microscope (e.g., a slit lamp) to identify the foreign body lodged in the eyelid.

Another fairly common instrument used to perform a double eyelid eversion is a scleral depressor, which is basically an elongated piece of metal with a single paddle at the end. Scleral depressors do not work well for performing double eyelid eversions because the single paddle at the end of the depressor does not hook onto the eyelid very effectively, and scleral depressors, like Desmarres retractors, are hard to use in the minimal space available when using a slit lamp.

U.S. Pat. No. 4,453,546 to Norman N. K. Katz et al. (hereinafter, "Katz et al."), titled "Scleral depressor", issued Jun. 12, 1984, and is incorporated herein by reference. Katz et al. describe an ophthalmic instrument for controlling eye position comprising a substantially oblong shaped blade that has a textured surface and that is formed with a hole substantially in the middle of the blade. In operation, the blade is manipulated by the operator to depress against the sclera of a patient's eye for either rotating or immobilizing the globe of the eye during examination. The instrument further comprises a handle, with optional pocket clip, which is attached to the blade at an offset angle to facilitate manipulation of the blade from a position that leaves the field substantially clear for the simultaneous use of other instruments, such as an ophthalmoscope.

U.S. Patent Application Publication US 2008/0081952 to Robert G. Josephberg (hereinafter, "Josephberg"), titled "SCLERAL DEPRESSOR", published Apr. 3, 2008, and is incorporated herein by reference. Josephberg describe a scleral depressor designed to better control the globe of the eye is disclosed. In a preferred embodiment, the scleral depressor has a handle and a blade attached to the handle where the blade is a portion of an oblate spheroid. In one embodiment, the blade has an illuminating device. The handle is attached to the blade at an angle or straight in relation to the plane of the handle. In another embodiment, the blade is attached to a thimble. In another embodiment of the invention, the blade has an access hole for simultaneous use of other instruments during examination or surgery. The resulting apparatus has greatly improved control of the eye, effective visualization of the periphery, ease of use for the examiner, and increased comfort for the patient.

There is a need for an improved apparatus and method for performing a double eyelid eversion, particularly a double eyelid eversion that can be performed while the patient is in front of a slit lamp during the search and removal of a foreign body from the upper eyelid of the patient.

BRIEF SUMMARY OF THE INVENTION

In some embodiments, the present invention provides a handheld medical instrument configured to double evert an eyelid of an animal, the instrument including an elongated handle member, wherein the handle member includes a first end and a second end; and a plurality of extensions, including a first extension and a second extension, that extend from a top surface of the first end of the handle member at an angle that is substantially perpendicular to a longitudinal axis of the handle member, wherein the plurality of extensions are configured to grasp the eyelid, wherein the first extension is located on a first side of the top surface of the handle member and the second extension is located on a second side of the top surface of the handle member, and wherein the first side is opposite the second side.

In some embodiments, the present invention provides a method for double everting an eyelid of an animal, the method including providing a handheld medical instrument that includes an elongated handle member, wherein the handle member includes a first end and a second end, and a plurality of extensions, including a first extension and a second extension, that extend from a top surface of the first end of the handle member at an angle that is substantially perpendicular to a longitudinal axis of the handle member, wherein the plurality of extensions are configured to grasp the eyelid, wherein the first extension is located on a first side of the top surface of the handle member and the second extension is located on a second side of the top surface of the handle member, and wherein the first side is opposite the second side, the method further including holding the eyelid to the second end of the handle member and rotating the medical instrument until the eyelid is placed in an everted position; moving the second end of the handle member away from the everted eyelid; positioning the plurality of extensions over a lower edge of the everted eyelid in order to grasp the everted eyelid with the plurality of extensions, wherein the positioning includes placing the first extension in front of the everted eyelid and placing the second extension behind the everted eyelid; and rotating the medical instrument until the grasped-everted eyelid is placed in a double-everted position.

BRIEF DESCRIPTION OF THE FIGURES

FIG. 3D is a schematic view of block 303 of FIG. 3A being performed by double eyelid everter 201.
FIG. 5B is a schematic view of block 302 of FIG. 3A being performed by double eyelid everter 401.

DETAILED DESCRIPTION OF THE INVENTION

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, the conjunctiva is a clear layer located in front of the sclera (i.e., the white part) of the eye.

Figure 1A:
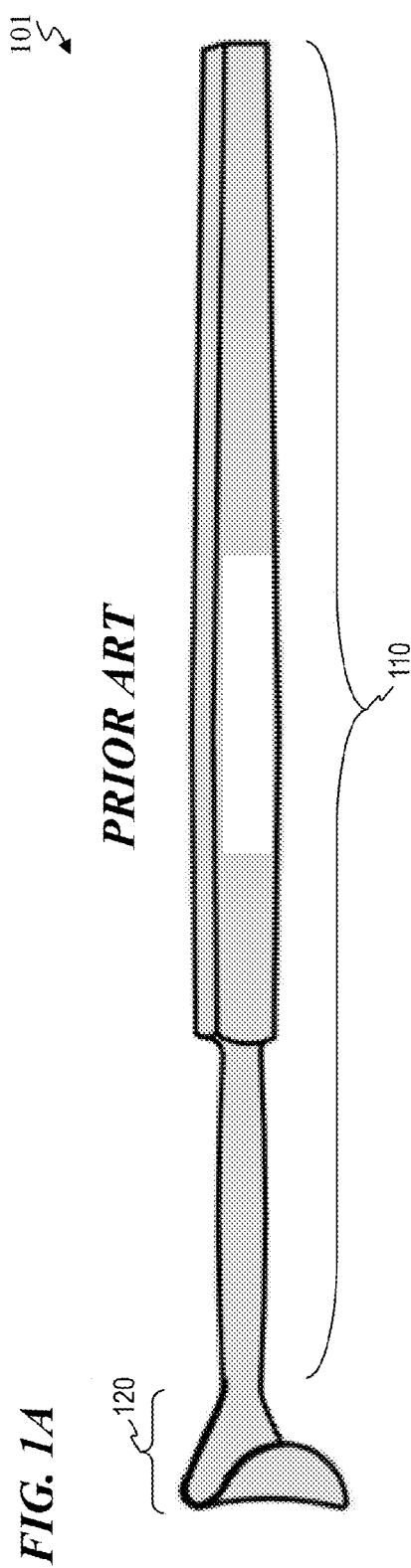
FIG. 1A is a perspective view of a Desmarres retractor 101.

FIG. 1A is a perspective view of a Desmarres retractor 101 such as found in the prior art. Desmarres retractor 101 includes an elongated handle member 110 and a flattened hook-like portion 120 at an end of the retractor 101. In some embodiments, Desmarres retractor 101 is used to perform a double eyelid eversion. In some such embodiments, an eye-care professional first performs an initial eyelid eversion as described above, and then the eye-care professional uses hook-like portion 120 to turn the tarsus skin surface of the eyelid inside out such that the fornix skin surface of the eyelid is exposed. As described above, a Desmarres retractor does not work well for performing a double eyelid eversion while the patient is in front of a slit lamp because hook-like portion 120 must be used such that handle member 110 comes out away from the patient in a manner substantially perpendicular to the surface of the patient's eyelid, which doesn't allow the slit lamp to be positioned close enough to the eye to obtain a useful image.

Figure 1B:
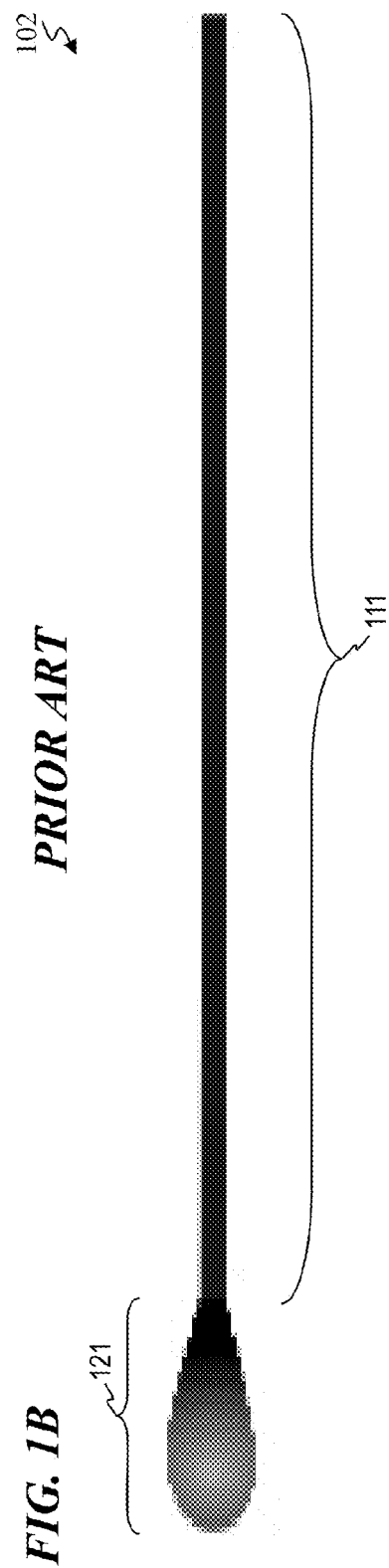
FIG. 1B is a plan view of a scleral depressor 102.

FIG. 1B is a plan view of a scleral depressor 102 such as found in the prior art. Scleral depressor 102 includes an elongated handle member 111 and a single paddle-shaped portion 121 at an end of the depressor 102. In some embodiments, scleral depressor 102 is used to perform a double eyelid eversion. In some such embodiments, an eye-care professional first performs an initial eyelid eversion as described above, and then the eye-care professional uses paddled-shaped portion 121 to turn the tarsus skin surface of the eyelid inside out such that the fornix skin surface of the eyelid is exposed. As described above, a scleral depressor does not work well for performing a double eyelid eversion because the single paddle-shaped portion 121 does not hook onto the eyelid very effectively, and scleral depressors, like Desmarres retractors, are hard to use in the minimal space available when using a slit lamp.

Figure 2A:
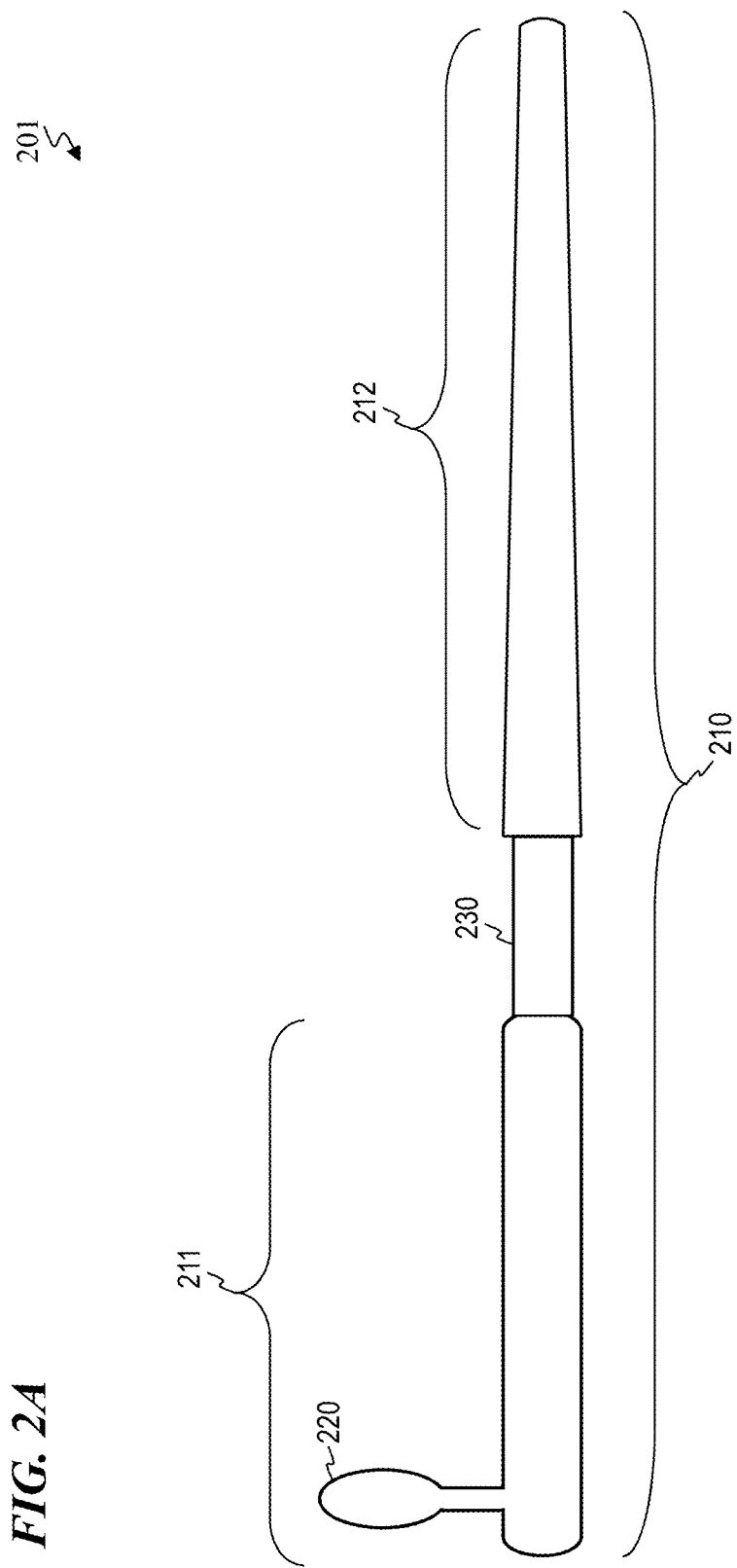
FIG. 2A is a schematic side view of a double eyelid everter 201.
Figure 2B:
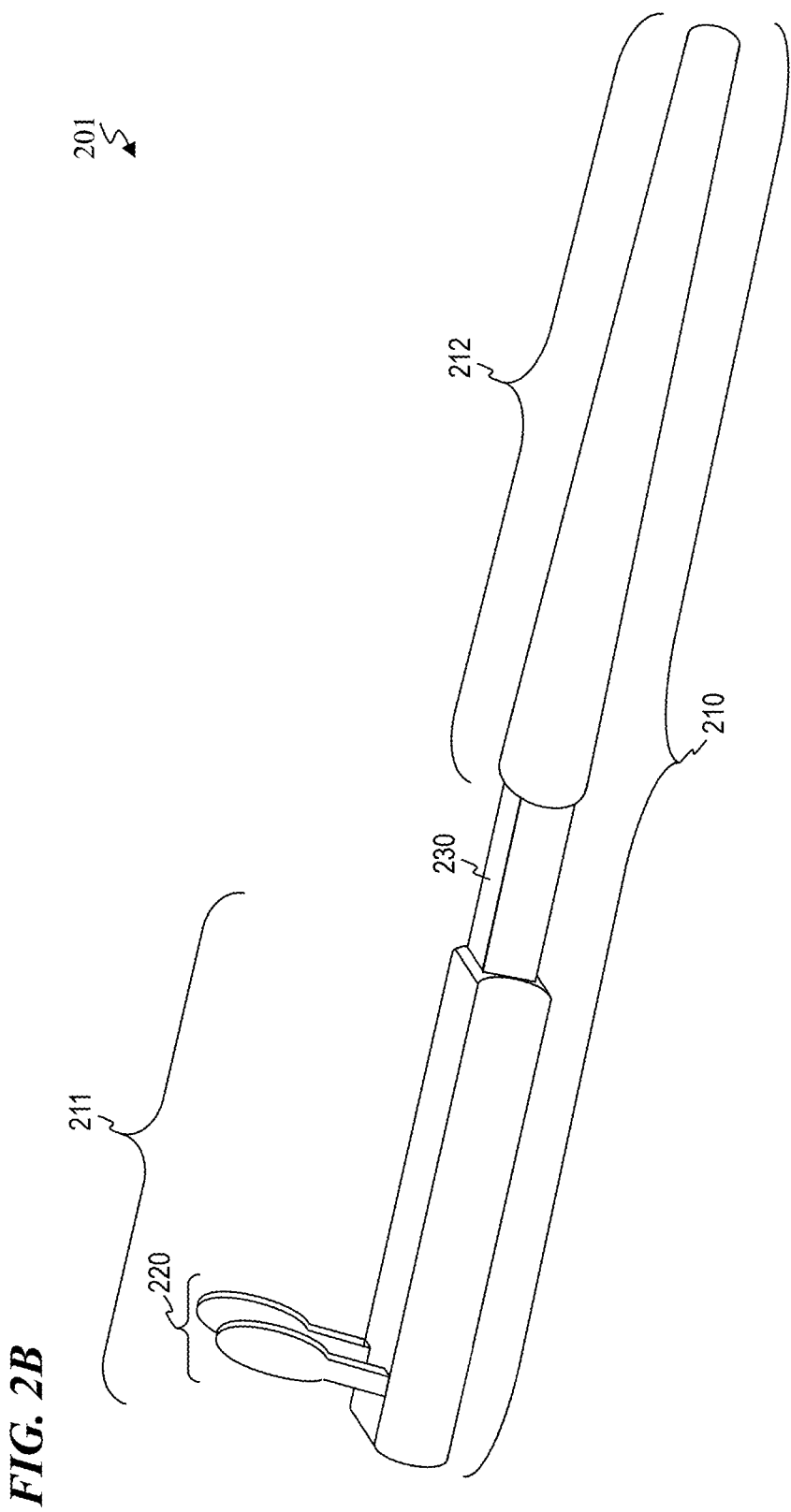
FIG. 2B is a schematic perspective view of double eyelid everter 201.

FIG. 2A is a schematic side view of a double eyelid everter 201. In some embodiments, double eyelid everter 201 is a small hand-held medical instrument configured to evert and then double evert an eyelid (e.g., an upper eyelid) of a patient. In some embodiments, double eyelid everter 201 includes an elongated handle member 210. In some embodiments, handle member 210 includes a first end 211 and a second end 212. In some embodiments, second end 212 of double eyelid everter 201 is smooth and rounded and configured to initially evert the patient's eyelid (see FIGS. 3A-3B). In some embodiments, as illustrated in FIGS. 2A and 2B, second end 212 tapers from a first diameter to a second diameter that is smaller than the first diameter. In other embodiments, second end 212 has a substantially constant diameter along the length of second end 212. In some embodiments, double eyelid everter 201 includes one or more extensions 220 coupled to handle member 210 at first end 211 of double eyelid everter 201, opposite second end 212. In some embodiments, the one or more extensions 220 extend from the top surface of handle member 210 at an angle that is substantially (or exactly) perpendicular to the longitudinal axis of handle member 210. In some embodiments, one or more extensions 220 are configured to double evert the initially everted eyelid of the patient (see FIGS. 3C-3D).

Figure 5A:
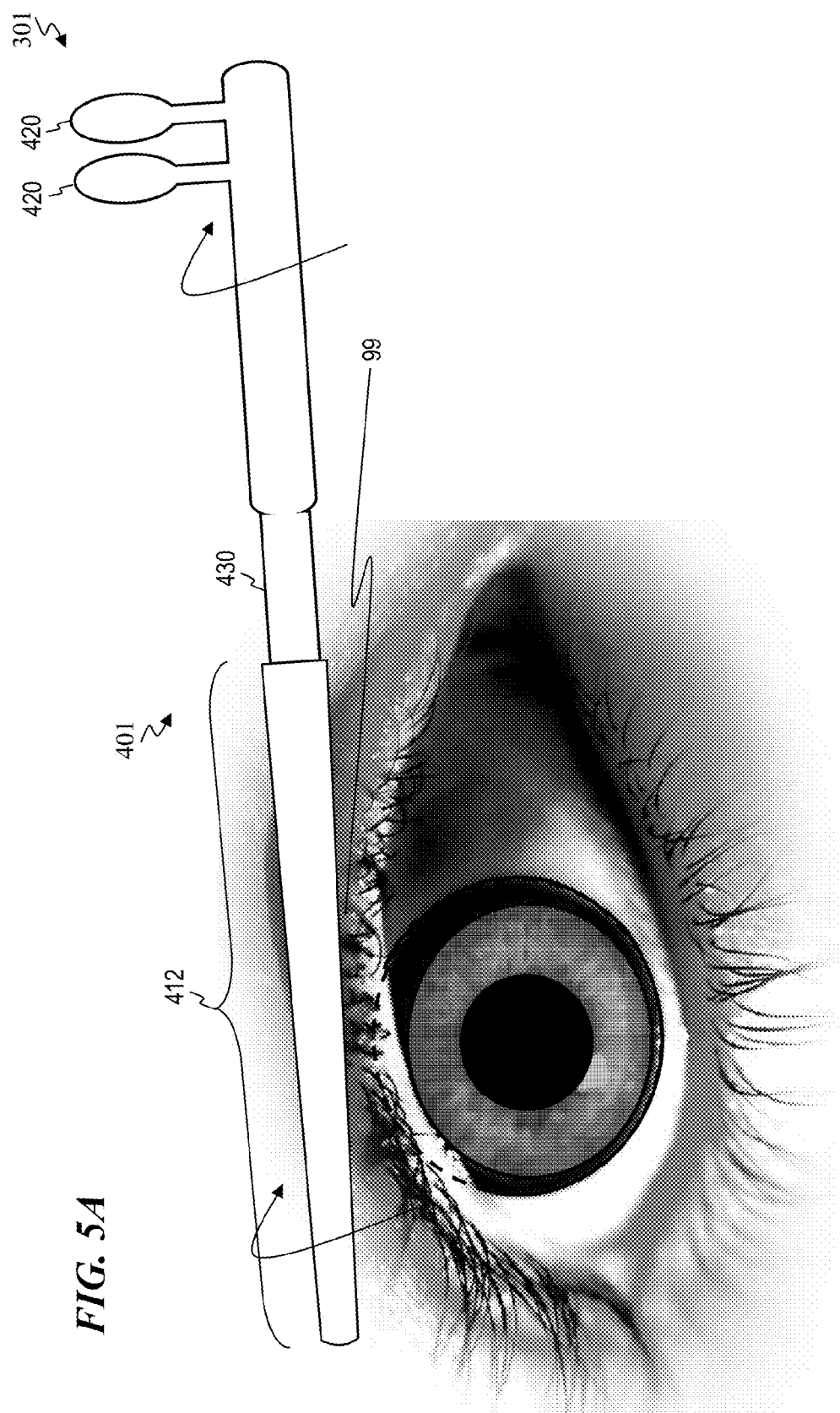
FIG. 5A is a schematic view of block 301 of FIG. 3A being performed by double eyelid everter 401.
Figure 5C:
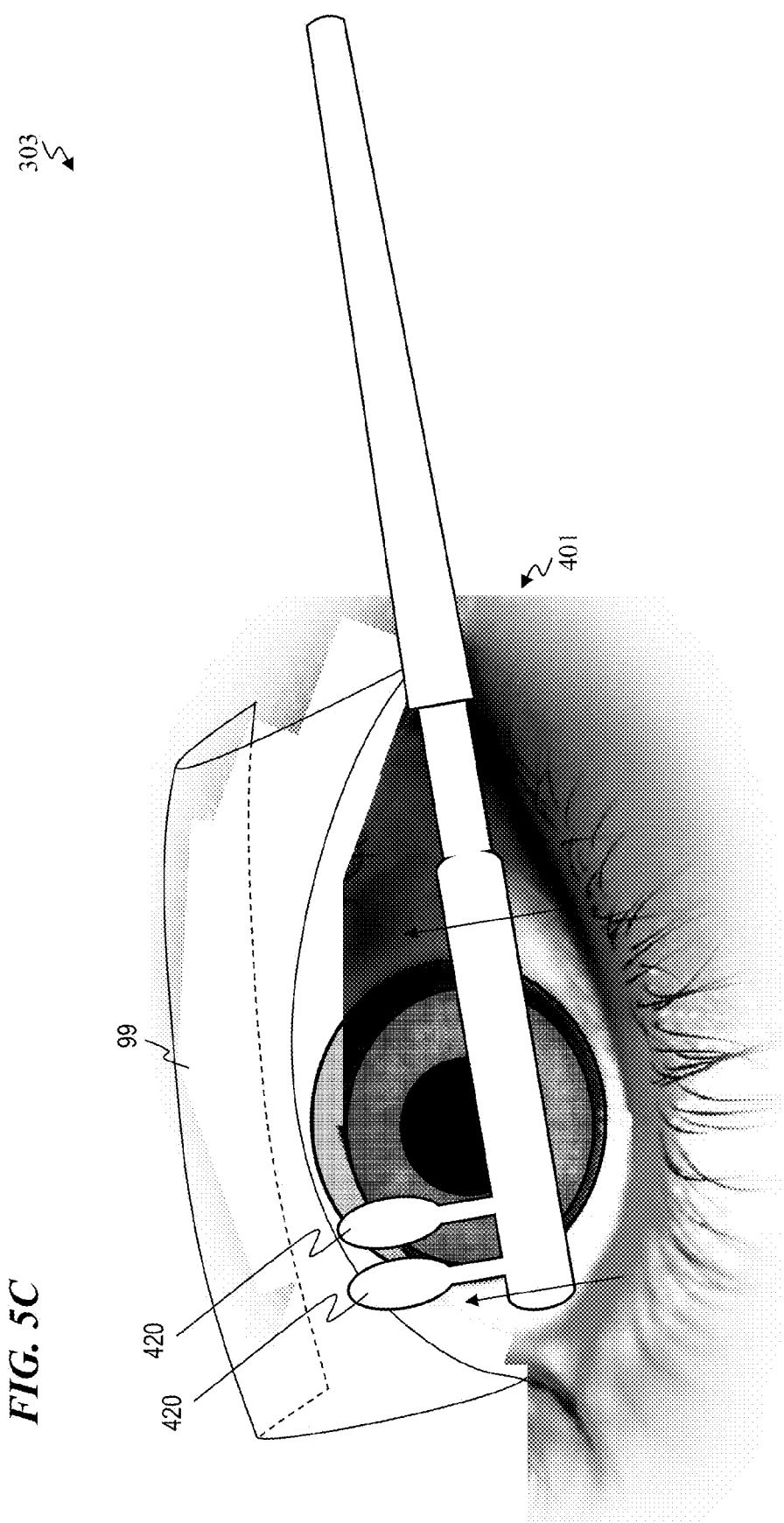
FIG. 5C is a schematic view of block 303 of FIG. 3A being performed by double eyelid everter 401.
Figure 5D:
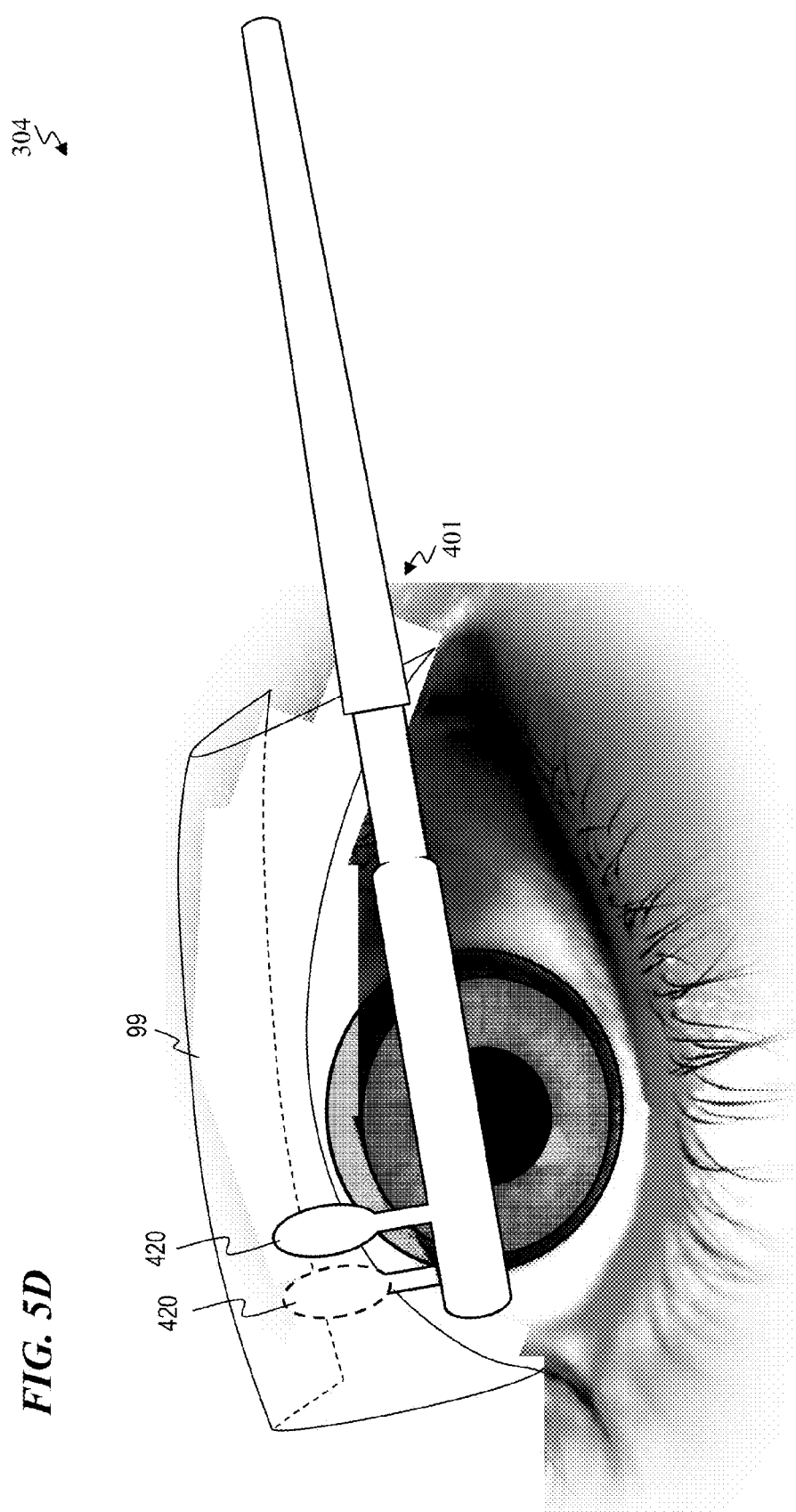
FIG. 5D is a schematic view of block 304 of FIG. 3A being performed by double eyelid everter 401.

In some embodiments, double eyelid everter 201 includes two extensions 220 that are configured to be slipped over the lower edge of the everted eyelid, one in front and one behind the eyelid (see FIGS. 3D and 5D). With extensions 220 in place over the lower edge of the everted eyelid, the eyelid can then be raised or double everted to expose the superior portion of the palpebral and bulbar conjunctiva as well as the fornix, in order to locate and remove foreign bodies lodged in the superior fornix. In some embodiments, since the longitudinal axis of double eye everter 201 is substantially parallel to the surface of the eyelid during use, double eye everter 201 can easily be used on the patient at the same time that the eye-care professional examines the patient's eye with a slit lamp. In other embodiments, double eye everter 201 is used with the patient supine on an exam table.

In some embodiments, double eyelid everter 201 includes a grip section 230 that is configured to provide a gripping surface for the user of double eyelid everter 201. In some embodiments, grip section 230 has a square cross-section. In other embodiments, grip section 230 has any other suitable cross-section shape. In some embodiments, grip section 230 includes a textured surface. In some embodiments, grip section 230 includes a tacky or sticky material. In some embodiments, as illustrated in FIG. 2A, grip section 230 has a smaller diameter than the other portions of handle member 210.

In some embodiments, double eyelid everter 201 is made from a material that includes stainless steel. In some such embodiments, double eyelid everter 201 is configured to be autoclaved between each patient such that everter 201 can be safely reused between patients. In some embodiments, double eyelid everter 201 is made from a material that includes a polymer. In some such embodiments, double eyelid everter 201 is configured to be disposed of after use with a single patient.

In some embodiments, as illustrated in FIG. 2A, extensions 220 are paddled-shaped (i.e., having a rectangular neck coupled to the top surface of the handle member at one end of the neck and a circle or oval-shaped portion coupled to the other end of the neck). In other embodiments, extensions 220 are any other suitable shape (e.g., square-shaped, rectangular, triangular, hexagonal, etc.). In some embodiments, extensions 220 have smooth edges such that extensions 220 can be slipped over the lower edge of an everted eyelid without damaging the eyelid. In some embodiments, each of the one or more extensions 220 is located approximately four millimeters (mm) from the edge of first end 211. In other embodiments, each of the one or more extensions 220 is located any other suitable distance from the edge of first end 211. In some embodiments, each of the one or more extensions 220 extends approximately six mm from handle member 210, each of the one or more extensions 220 is approximately three mm wide, and each of the one or more extensions 220 has a depth of approximately one mm (in some such embodiments the one or more extensions 220 are paddle-shaped and the base of an individual paddle is approximately a third of the height of the overall height of the individual paddle; in other embodiments, the base of an individual paddle is any other suitable height). In some embodiments, each of the one or more extensions 220 extends more than six mm from handle member 210. In other embodiments, each of the one or more extensions 220 extends less than six mm from handle member 210. In some embodiments, each of the one or more extensions 220 is more than three mm wide. In other embodiments, each of the one or more extensions 220 is less than three mm wide. In some embodiments, each of the one or more extensions 220 has a depth of less than one mm. In other embodiments, each of the one or more extensions 220 has a depth of more than one mm.

In some embodiments, a first one of the one or more extensions 220 extends from handle member 210 at a first distance, and a second one of the one or more extensions 220 extends from handle member 210 at a second distance that is longer than the first distance. In some embodiments, the one or more extensions 220 include a first extension 220 and a second extension 220, and first extension 220 has a first width and a first depth, and second extension 220 has a second width and a second depth that are different than the first width and the first depth.

In some embodiments, handle member 210 has a length of approximately 100 mm. In some embodiments, handle member 210 has a length of between about 75 mm and about 80 mm. In some embodiments, handle member 210 has a length of less than 75 mm. In some embodiments, handle member 210 has a length of between about 80 mm and about 85 mm, a length of between about 85 mm and about 90 mm, a length of between about 90 mm and about 95 mm, a length of between about 95 mm and about 100 mm, a length of between about 100 mm and about 105 mm, a length of between about 105 mm and about 110 mm, a length of between about 110 mm and about 115 mm, a length of between about 115 mm and about 120 mm, a length of between about 120 mm and about 125 mm, a length of between about 125 mm and about 130 mm, a length of between about 130 mm and about 140 mm, a length of between about 140 mm and about 150 mm, a length of between about 150 mm and about 160 mm, a length of between about 160 mm and about 170 mm, a length of between about 170 mm and about 180 mm, a length of between about 180 mm and about 190 mm, or a length of between about 190 mm and about 200 mm. In some embodiments, handle member 210 has a length of greater than 200 mm.

FIG. 2B is a schematic perspective view of double eyelid everter 201. In some embodiments, as illustrated in FIG. 2B, double eyelid everter 201 includes two extensions 220, wherein a first one of the two extensions 220 is located on a first side of double eyelid everter 201 and a second one of the two extensions 220 is located on a second side of double eyelid everter 201. In some embodiments, the two individual extensions 220 are directly aligned with each other across the top surface of handle member 210 such that only one of the two extensions 220 can be seen from a side view of double eyelid everter 201 (see, e.g., FIG. 2A). In some such embodiments, extensions 220 are separated from each other on the top surface of handle member 210 by a distance of approximately four mm. In other embodiments, extensions 220 are separated from each other on the top surface of handle member 210 by any other suitable distance.

Figure 3A:
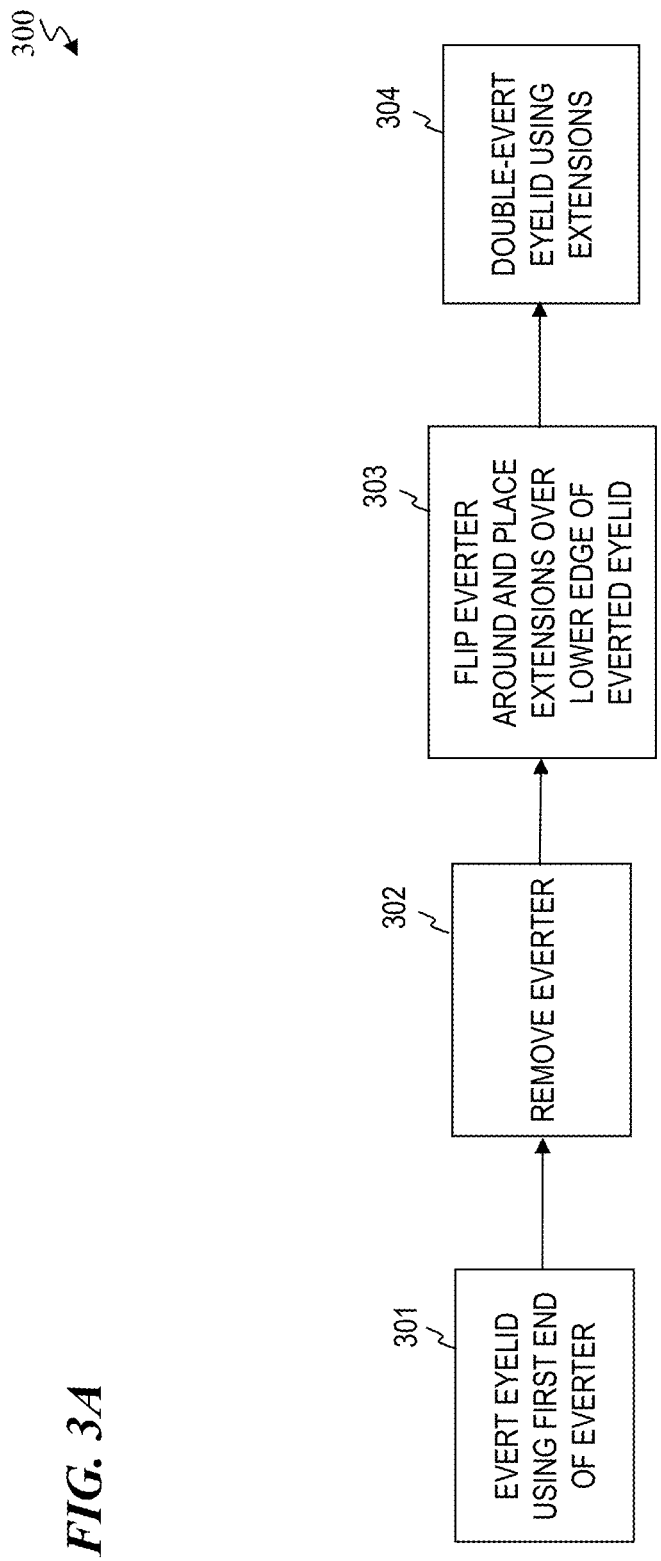
FIG. 3A is a block diagram of a method for a double eyelid eversion 300 according to some embodiments of the present invention.

FIG. 3A is a block diagram of a method for a double eyelid eversion 300 according to some embodiments of the present invention. In some embodiments, double eyelid eversion 300 includes everting the eyelid using a first end of a double eyelid everter of the present invention in block 301, removing the everter from the everted eyelid in block 302, flipping the everter around and placing the extensions of the everter over the lower edge of the everted eyelid in block 303, and double everting the everted eyelid using the extensions in block 304. In some embodiments, the method for double eyelid eversion 300 shown in FIG. 3A is used to double evert a lower eyelid.

Figure 3B:
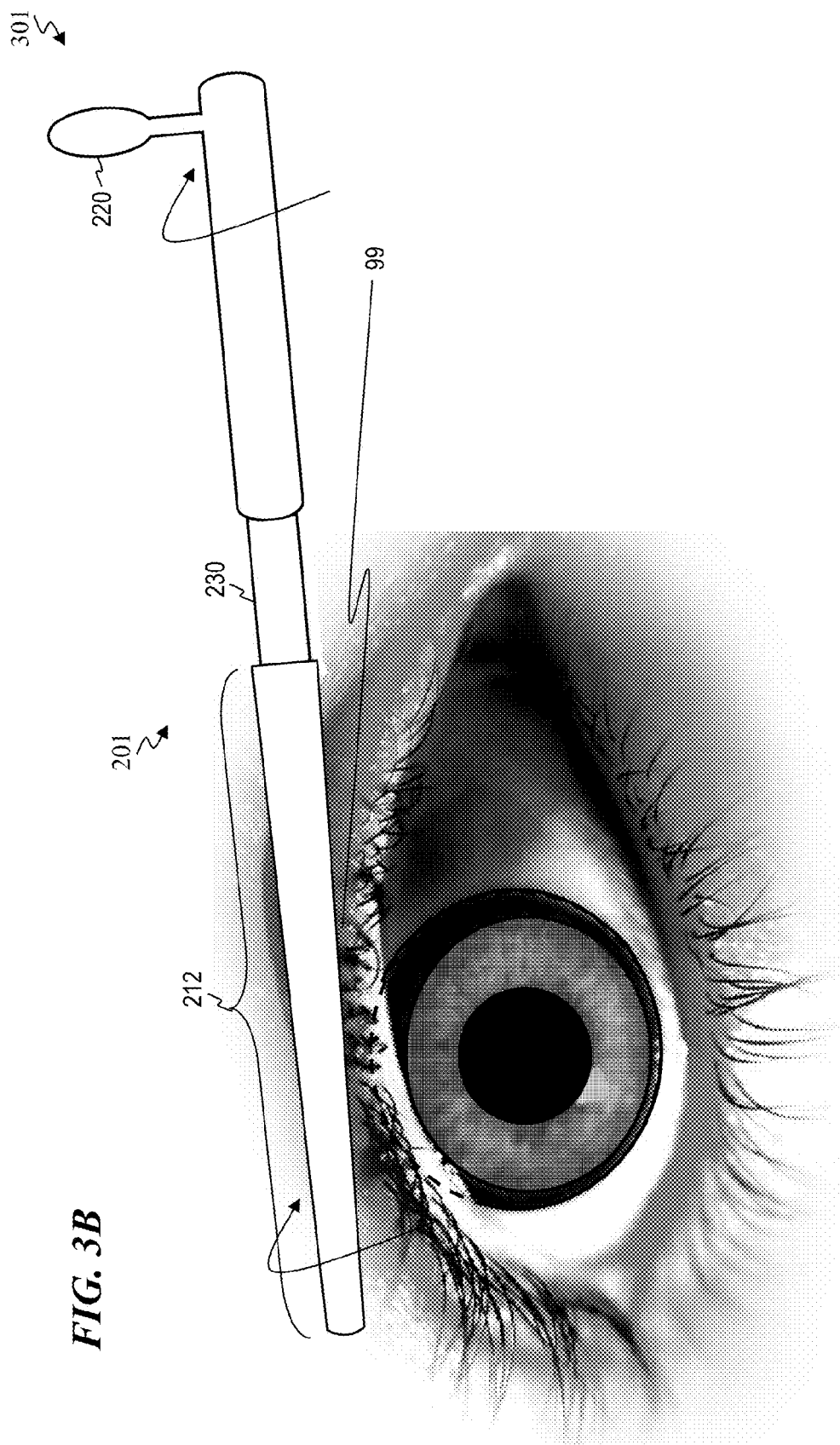
FIG. 3B is a schematic view of block 301 of FIG. 3A being performed by double eyelid everter 201.

FIG. 3B is a schematic view of block 301 of FIG. 3A being performed by double eyelid everter 201. In some embodiments, the double eyelid eversion is performed on the upper eyelid 99 of the patient. In some embodiments, second end 212 of double eyelid everter 201 is used to initially evert eyelid 99 by placing second end 212 on upper eyelid 99, holding the eyelashes of eyelid 99 to second end 212, and rotating double eyelid everter 201 in a clockwise direction such that eyelid 99 everts and exposes the palpebral conjunctiva.

Figure 3C:
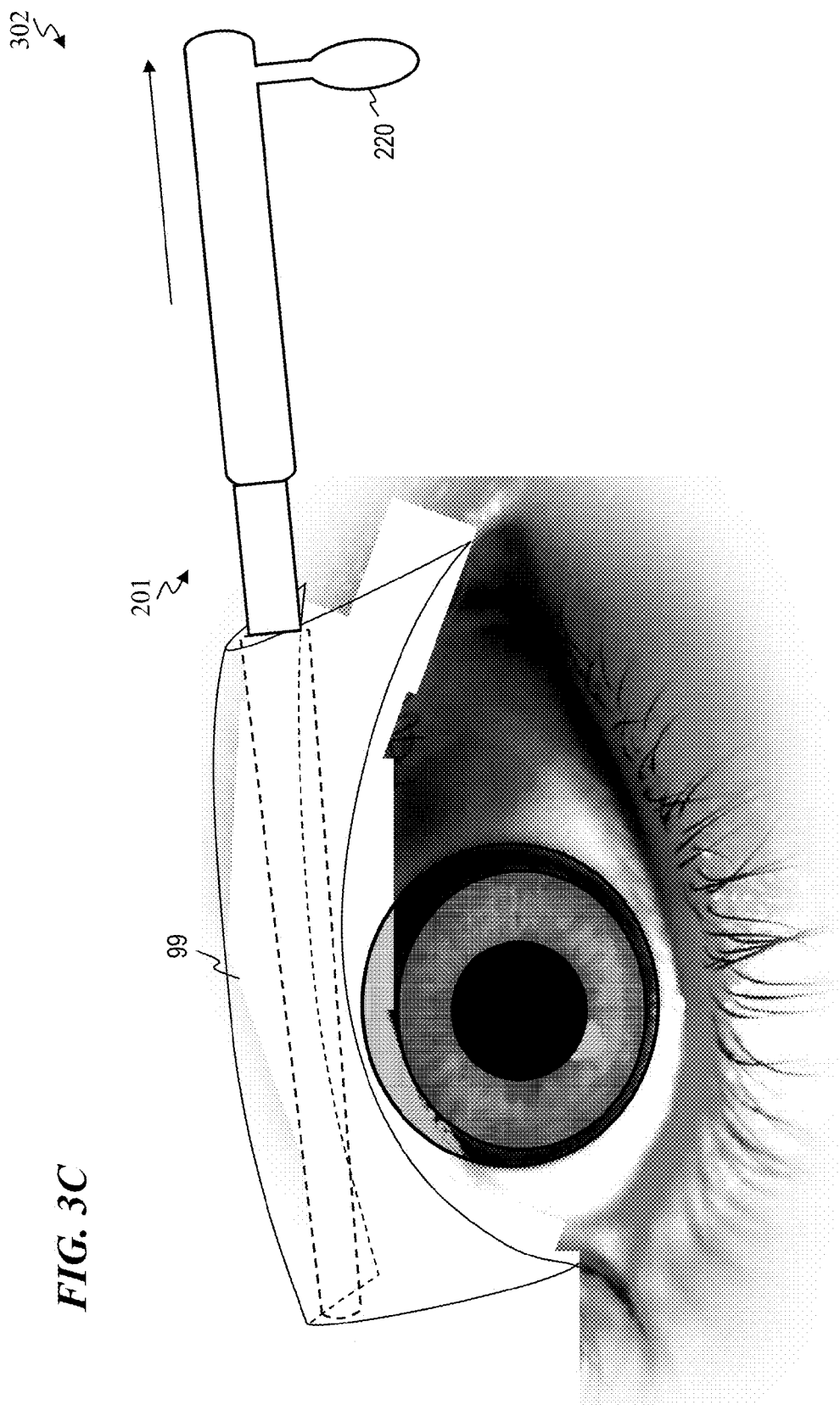
FIG. 3C is a schematic view of block 302 of FIG. 3A being performed by double eyelid everter 201.

FIG. 3C is a schematic view of block 302 of FIG. 3A being performed by double eyelid everter 201. In some embodiments, second end 212 of double eyelid everter 201 is gently pulled out from the everted eyelid 99. In some such embodiments, eyelid 99 is held in place by the eye-care professional during the removal of second end 212 to prevent eyelid 99 from flipping back to its normal position.

FIG. 3D is a schematic view of block 303 of FIG. 3A being performed by double eyelid everter 201. In some embodiments, double eyelid everter 201 is flipped around such that extensions 220 are directly in front of the patient's eye, and then extensions 220 are slipped up and over the lower edge of the everted eyelid 99, one extension 220 (visible in FIG. 3C) in front of eyelid 99 and one extension 220 (not visible in FIG. 3C) behind eyelid 99.

Figure 3E:
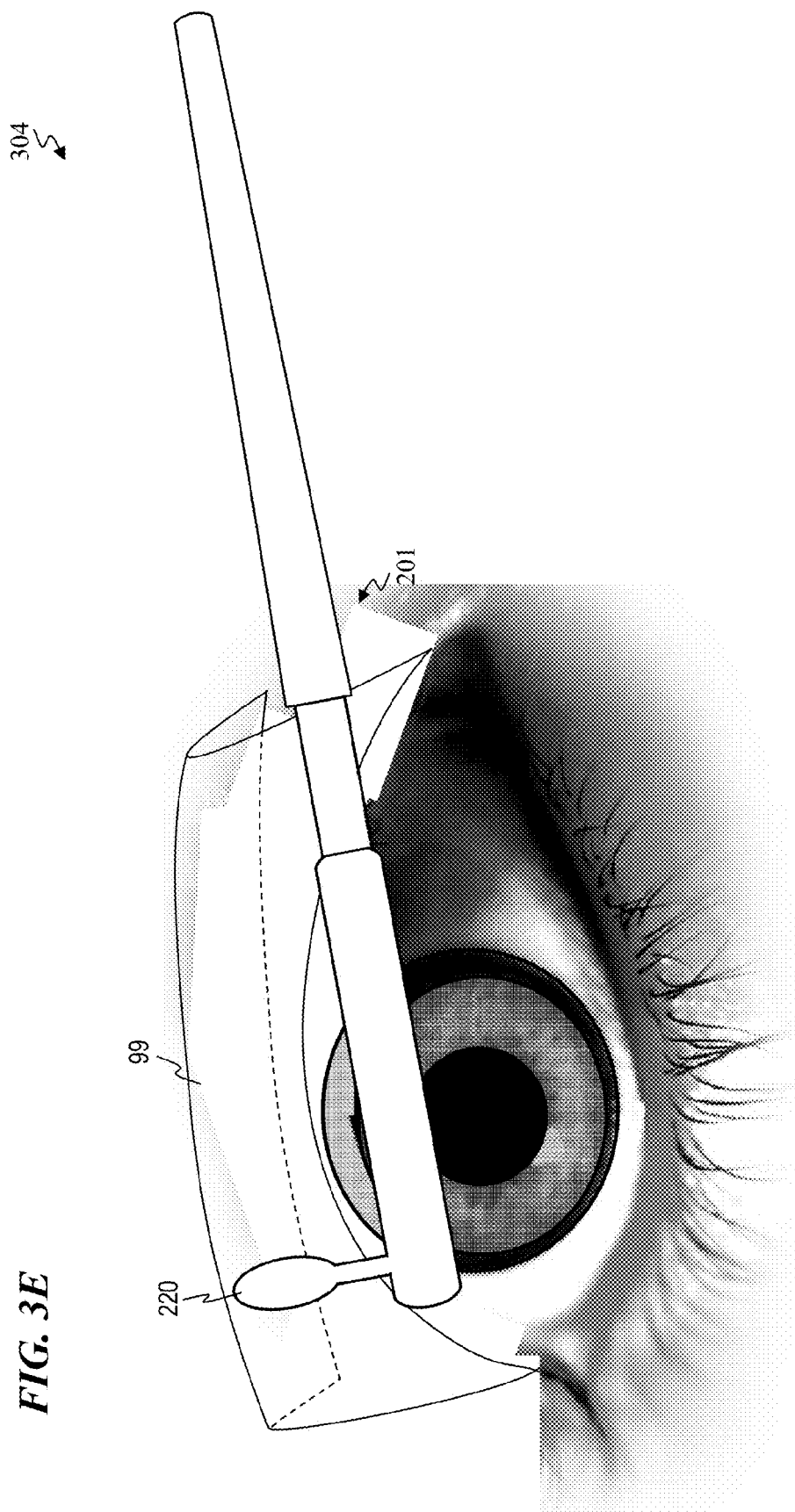
FIG. 3E is a schematic view of block 304 of FIG. 3A being performed by double eyelid everter 201.

FIG. 3E is a schematic view of block 304 of FIG. 3A being performed by double eyelid everter 201. In some embodiments, with extensions 220 in place over the lower edge of everted eyelid 99, eyelid 99 is raised or double everted to expose the superior portion of the palpebral and bulbar conjunctiva as well as the fornix, in order to locate and remove foreign bodies lodged in the superior fornix.

Figure 4A:
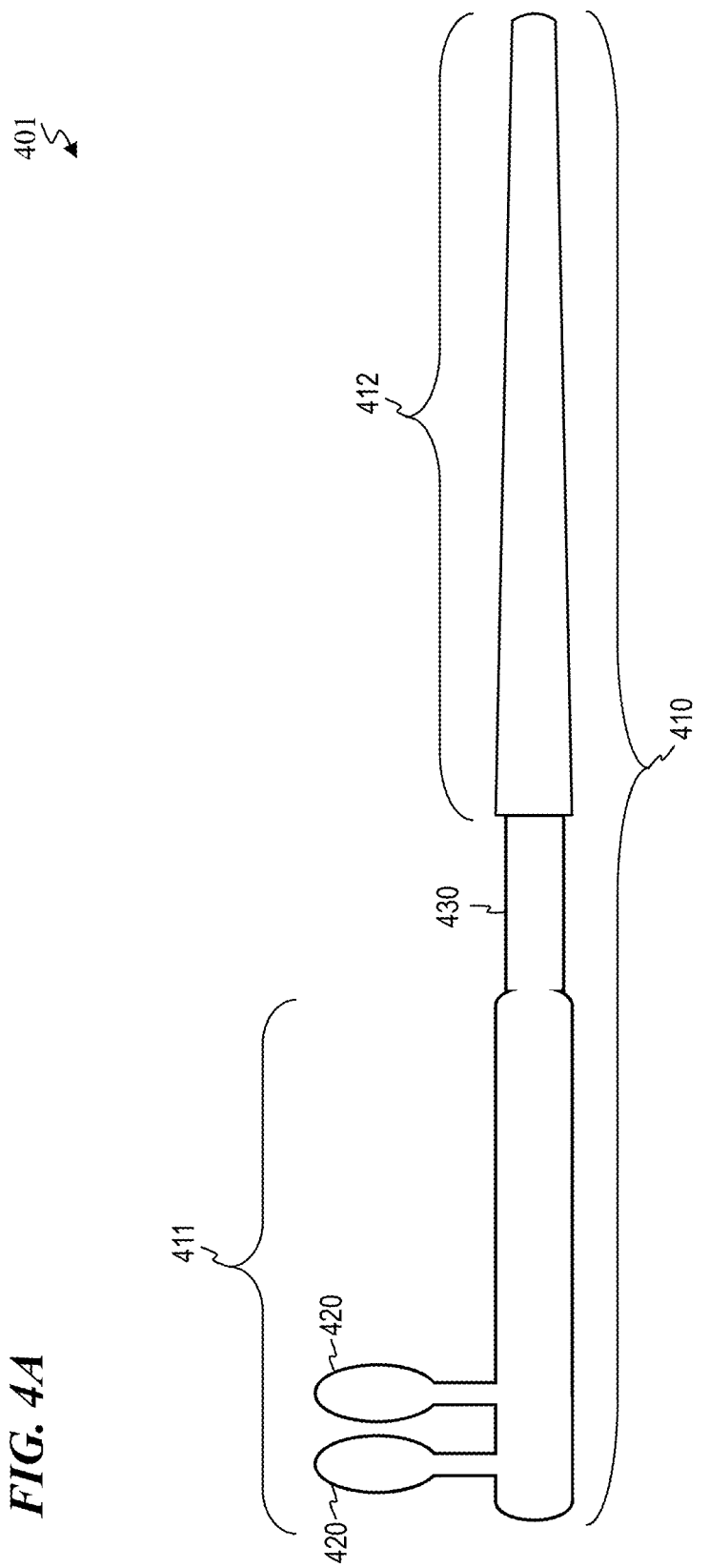
FIG. 4A is a schematic side view of a double eyelid everter 401.

FIG. 4A is a schematic side view of a double eyelid everter 401. In some embodiments, double eyelid everter 401 is substantially similar to double eyelid everter 201 except that the two individual extensions 420 on double eyelid everter 401 are not aligned directly across from each other on the top surface of handle member 410. In some embodiments, a first extension 420 is located approximately four millimeters from an edge of first end 411 and a base of a second extension 420 is longitudinally separated from a base of the first extension 420 by approximately 3 millimeters (in other embodiments, the longitudinally offset extensions 420 are located at any other suitable locations on the top surface of handle member 410). In some embodiments, in a manner similar to second end 212 of FIGS. 2A and 2B, second end 412 tapers from a first diameter to a second diameter that is smaller than the first diameter. In other embodiments, second end 412 has a substantially constant diameter along the length of second end 412. In some embodiments, double eyelid everter 401 includes a grip section 430 that is configured to provide a gripping surface for the user of double eyelid everter 401 (in some embodiments, grip section 430 is substantially similar to grip section 230 of FIGS. 2A and 2B).

Figure 4B:
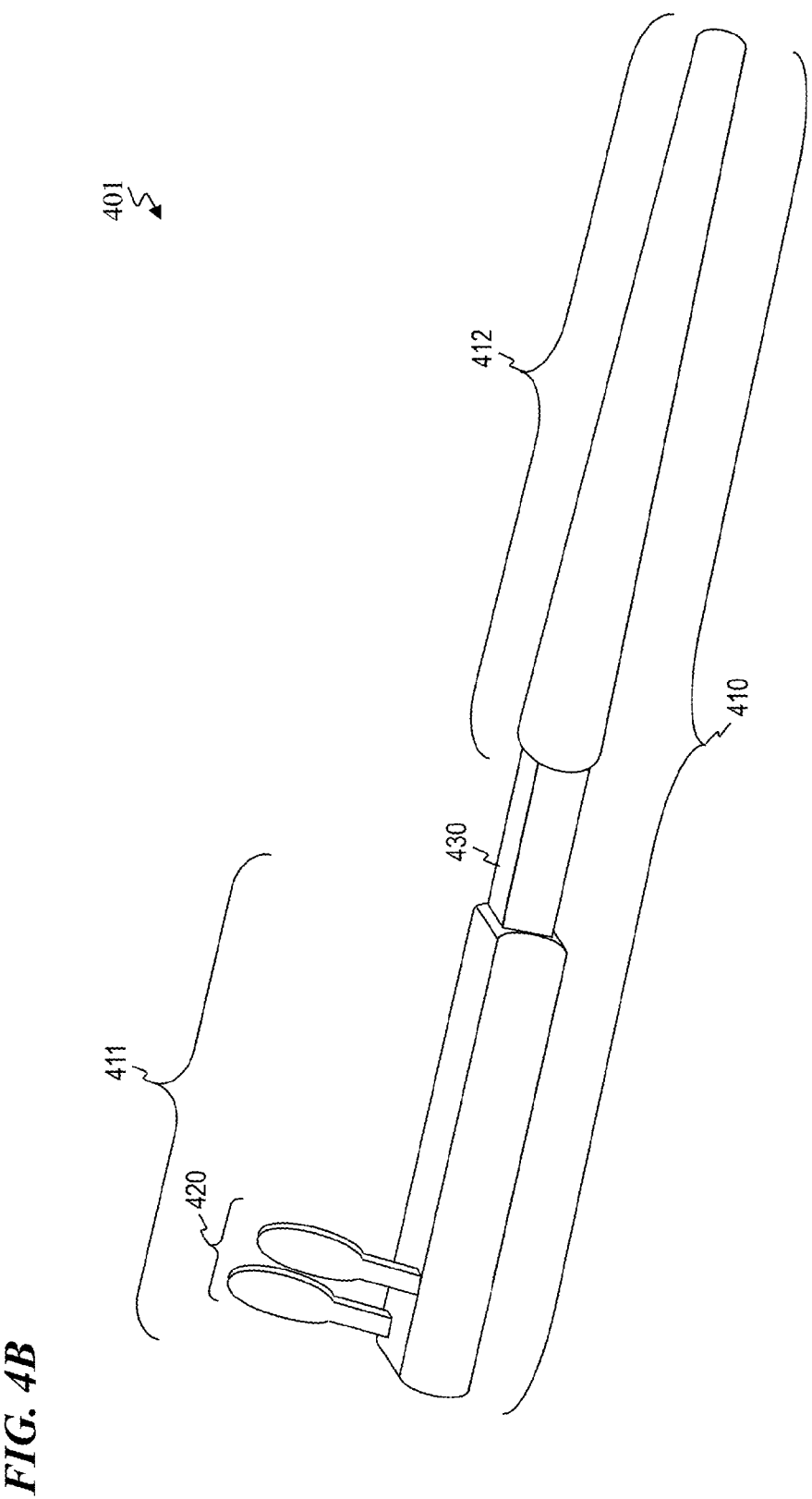
FIG. 4B is a schematic perspective view of double eyelid everter 401.

FIG. 4B is a schematic perspective view of double eyelid everter 401. In some embodiments, a first one of the two extensions 420 is located on a first side of double eyelid everter 401 and a second one of the two extensions 220 is located on a second side of double eyelid everter 401. In some embodiments, the two individual extensions 420 are offset from each other across the top surface of handle member 410 such that both of the two extensions 420 can be seen from a side view of double eyelid everter 401 (see, e.g., FIG. 4A).

FIG. 5A is a schematic view of block 301 of FIG. 3A being performed by double eyelid everter 401. In some embodiments, the double eyelid eversion is performed on the upper eyelid 99 of the patient. In some embodiments, first end 411 of double eyelid everter 401 is used to initially evert eyelid 99 by placing first end 411 on upper eyelid 99, holding the eyelashes of eyelid 99 to first end 411, and rotating double eyelid everter 401 in a clockwise direction such that eyelid 99 everts and exposes the palpebral conjunctiva.

FIG. 5B is a schematic view of block 302 of FIG. 3A being performed by double eyelid everter 401. In some embodiments, first end 411 of double eyelid everter 401 is gently pulled out from the everted eyelid 99. In some such embodiments, eyelid 99 is held in place by the eye-care professional during the removal of first end 411 to prevent eyelid 99 from flipping back to its normal position.

FIG. 5C is a schematic view of block 303 of FIG. 3A being performed by double eyelid everter 401. In some embodiments, double eyelid everter 401 is flipped around such that extensions 420 are directly in front of the patient's eye, and then extensions 420 are slipped up and over the lower edge of the everted eyelid 99, one extension 420 in front of eyelid 99 (e.g., the extension 420 on the right in FIG. 5D) and one extension 420 behind eyelid 99 (e.g., the extension 420 on the left in FIG. 5D).

FIG. 5D is a schematic view of block 304 of FIG. 3A being performed by double eyelid everter 401. In some embodiments, with extensions 420 in place over the lower edge of everted eyelid 99, eyelid 99 is raised or double everted to expose the superior portion of the palpebral and bulbar conjunctiva as well as the fornix, in order to locate and remove foreign bodies lodged in the superior fornix.

In some embodiments, the present invention provides a handheld medical instrument configured to double evert an eyelid of an animal, the instrument including an elongated handle member, wherein the handle member includes a first end and a second end; and a plurality of extensions including a first extension and a second extension, wherein the plurality of extensions are configured to hold an eyelid, wherein the plurality of extensions are coupled to the first end of the handle member, wherein the plurality of extensions extend from a top surface of the handle member at an angle that is substantially perpendicular to a longitudinal axis of the handle member, and wherein the first extension is located on a first side of the top surface of the handle member and the second extension is located on a second side of the top surface of the handle member.

In some embodiments of the instrument, the first end of the handle member has a first diameter, and wherein the second end of the handle member is rounded and tapers from the first diameter to a second diameter that is smaller than the first diameter. In other embodiments, the first end and the second end of the handle member have a first diameter.

In some embodiments of the instrument, the first extension and the second extension are located at a first location along the longitudinal axis of the handle member such that the first extension and the second extension are directly across from one another on the top surface of the handle member. In other embodiments, the first extension is located at a first location along the longitudinal axis of the handle member, and the second extension is located at a second location along the longitudinal axis of the handle member such that the first extension is longitudinally offset from the second extension.

In some embodiments of the instrument, wherein the handle member includes a grip portion configured to provide a location to grip the medical instrument, and wherein the grip portion is located between the first end and the second end of the handle member. In some embodiments, the grip portion has a textured surface. In some embodiments, the grip portion has a square cross-section. In some embodiments, the first end of the handle member has a first diameter, wherein the second end of the handle member is rounded and tapers from the first diameter to a second diameter that is smaller than the first diameter, and the grip portion has a third diameter that is smaller than the first diameter.

In some embodiments of the instrument, the medical instrument is made from a material that includes stainless steel, and the medical instrument is configured to be autoclaved between uses of the instrument. In some embodiments, the medical instrument is made from a material that includes a polymer, and wherein the medical instrument is configured to be disposed of after a single use.

In some embodiments of the instrument, each one of the plurality of extensions has a paddle shape such that the first extension has a narrow rectangular neck coupled to the top surface of the handle member at one end of the first extension and an oval-shaped segment coupled to the opposite end of the first extension. In some embodiments, each one of the plurality of extensions has a square shape.

In some embodiments, the present invention provides a method for double everting an eyelid, the method including providing a handheld eyelid everter that includes an elongated handle member, wherein the handle member includes a first end and a second end, and a plurality of extensions including a first extension and a second extension, wherein the plurality of extensions are configured to hold an eyelid, wherein the plurality of extensions are coupled to the first end of the handle member, wherein the plurality of extensions extend from a top surface of the handle member at an angle that is substantially perpendicular to a longitudinal axis of the handle member, and wherein the first extension is located on a first side of the top surface of the handle member and the second extension is located on a second side of the top surface of the handle member; everting the eyelid using the second end of the handle member; positioning the plurality of extensions over a lower edge of the everted eyelid such that the first extension is in front of the everted eyelid and the second extension is behind the everted eyelid; and double everting the everted eyelid using the plurality of extensions.

In some embodiments of the method, the everting includes placing the second end of the handle member on the eyelid, holding eyelashes of the eyelid to the second end, and rotating the eyelid everter such that the eyelid everts. In some embodiments, the positioning of the plurality of extensions includes removing the second end of the handle member from the everted eyelid and flipping the eyelid everter around such that the plurality of extensions is next to the eyelid. In some embodiments, the removing of the second end of the handle member from the everted eyelid includes holding the everted eyelid in place in order to prevent the everted eyelid from returning to a normal position while removing the second end. In some embodiments, the double everting includes pulling the lower edge of the everted eyelid up using the plurality of extensions.

In some embodiments, the method further includes providing a grip portion between the first end and the second end of the handle member; and gripping the eyelid everter at the grip portion while the method is performed.

In some embodiments, the present invention provides a handheld eyelid everter that includes means for everting an eyelid; and means for double everting the everted eyelid.

In some embodiments, the present invention provides a handheld medical instrument configured to double evert an eyelid of an animal, the instrument including an elongated handle member, wherein the handle member includes a first end and a second end; and a plurality of extensions, including a first extension and a second extension, that extend from a top surface of the first end of the handle member at an angle that is substantially perpendicular to a longitudinal axis of the handle member, wherein the plurality of extensions are configured to grasp the eyelid, wherein the first extension is located on a first side of the top surface of the handle member and the second extension is located on a second side of the top surface of the handle member, and wherein the first side is opposite the second side.

In some embodiments of the medical instrument, the first end of the handle member has a first diameter, and wherein the second end of the handle member is rounded and tapers from the first diameter to a second diameter that is smaller than the first diameter. In some embodiments, the first end and the second end of the handle member have a first diameter.

In some embodiments of the medical instrument, the first extension and the second extension are both located at a first longitudinal position along the longitudinal axis of the handle member such that the first extension and the second extension are located directly across from one another on the top surface of the handle member. In other embodiments, the first extension is located at a first longitudinal position along the longitudinal axis of the handle member, and wherein the second extension is located at a second longitudinal position along the longitudinal axis of the handle member such that the first extension is longitudinally offset from the second extension.

In some embodiments of the medical instrument, the handle member includes a grip portion configured to provide a location to grip the medical instrument, and wherein the grip portion is located between the first end and the second end of the handle member. In some embodiments, the grip portion has a textured surface. In some embodiments, the grip portion has a square cross-section.

In some embodiments of the medical instrument, the first end of the handle member has a first diameter, wherein the second end of the handle member is rounded and tapers from the first diameter to a second diameter that is smaller than the first diameter, and wherein the grip portion has a third diameter that is smaller than the first diameter.

In some embodiments of the medical instrument, the medical instrument is made from a material that includes stainless steel, wherein the medical instrument is configured to be autoclaved between uses of the instrument. In some embodiments, the medical instrument is made from a material that includes a polymer, wherein the medical instrument is configured to be disposed of after a single use.

In some embodiments of the medical instrument, each one of the plurality of extensions has a handle end that couples to the top surface of the handle member and a distal end that is located at a distance away from the handle member, wherein each one of the plurality of extensions has a paddle shape such that the first extension includes a rectangular neck at the handle end of the first extension and an oval-shaped segment coupled to the rectangular neck at the distal end of the first extension. In some embodiments, each one of the plurality of extensions has a square shape. In some embodiments, each one of the plurality of extensions has a rectangular shape.

In some embodiments, the present invention provides a method for double everting an eyelid of an animal, the method including providing a handheld medical instrument that includes: an elongated handle member, wherein the handle member includes a first end and a second end, and a plurality of extensions, including a first extension and a second extension, that extend from a top surface of the first end of the handle member at an angle that is substantially perpendicular to a longitudinal axis of the handle member, wherein the plurality of extensions are configured to grasp the eyelid, wherein the first extension is located on a first side of the top surface of the handle member and the second extension is located on a second side of the top surface of the handle member, and wherein the first side is opposite the second side; the method further including placing the second end of the handle member across the eyelid; holding an edge of the eyelid to the second end of the handle member and rotating the everter until the eyelid is placed in an everted position; moving the second end of the handle member away from the everted eyelid; positioning the plurality of extensions over a lower edge of the everted eyelid in order to grasp the everted eyelid with the plurality of extensions, wherein the positioning includes placing the first extension in front of the everted eyelid and placing the second extension behind the everted eyelid; and lifting the grasped-everted eyelid upward and outward by rotating the everter until the eyelid is placed in a double-everted position.

In some embodiments of the method, the everting of the eyelid by holding an edge of the eyelid to the second end of the handle member includes holding eyelashes of the eyelid to the second end of the handle member.

In some embodiments of the method, the animal is a human, wherein the eyelid is coupled to an eye of the human, wherein a portion of the eye that is normally covered by the eyelid becomes exposed when the eyelid is placed in the double-everted position, and wherein the method further includes providing a slit lamp; and observing, using the slit lamp, the exposed portion of the eye. In some embodiments, the animal is a human, wherein the eyelid is coupled to an eye of the human, wherein a portion of the eye that is normally covered by the eyelid becomes exposed when the eyelid is placed in the double-everted position, and wherein the method further includes removing a foreign body from the exposed portion of the eye.

In some embodiments of the method, the removing of the second end of the handle member away from the everted eyelid includes holding the everted eyelid in the everted position in order to prevent the everted eyelid from returning to a non-everted position while removing the second end of the handle member.

In some embodiments of the method, the handheld medical instrument is made from a material that includes stainless steel, and the method further includes autoclaving the medical instrument between uses of the medical instrument. In some embodiments, the handheld medical instrument is made from a material that includes a polymer, and the method further includes disposing the medical instrument after a single use.

In some embodiments, the present invention provides a handheld medical instrument that includes means for double-everting an eyelid.

In some embodiments, the present invention provides a handheld medical instrument that includes means for everting an eyelid; and means for double-everting the everted eyelid.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment). Further, some embodiments include fewer than all the components described as part of any one of the embodiments described herein.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A handheld medical instrument configured to double evert an eyelid of an animal, the instrument comprising:
   an elongated handle member, wherein the handle member includes a first end and a second end, wherein the handle member has an end-to-end length, and wherein the handle member has a longitudinal axis that contacts the handle member along an entirety of the end-to-end length of the handle member; and
   a plurality of extensions, including a first extension and a second extension, that extend from a top surface of the first end of the handle member at an angle that is substantially perpendicular to the longitudinal axis of the handle member, wherein the first extension is in a fixed position relative to the second extension, wherein the first extension is located on a first side of the top surface of the first end and the second extension is located on a second side of the top surface of the first end, wherein the first side is opposite the second side, wherein the first extension is located at a first longitudinal position along the longitudinal axis of the handle member, and wherein the second extension is located at a second longitudinal position along the longitudinal axis of the handle member such that the first extension is longitudinally offset from the second extension.

2. The medical instrument of claim 1, wherein the first end of the handle member has a first diameter, and wherein the second end of the handle member is rounded and tapers from the first diameter to a second diameter that is smaller than the first diameter.

3. The medical instrument of claim 1, wherein the first end and the second end of the handle member have a first diameter.

4. The medical instrument of claim 1, wherein the handle member includes a grip portion configured to provide a location to grip the medical instrument, and wherein the grip portion is located between the first end and the second end of the handle member.

5. The medical instrument of claim 4, wherein the grip portion has a textured surface.

6. The medical instrument of claim 4, wherein the grip portion has a square cross-section.

7. The medical instrument of claim 4, wherein the first end of the handle member has a first diameter, wherein the second end of the handle member is rounded and tapers from the first diameter to a second diameter that is smaller than the first diameter, and wherein the grip portion has a third diameter that is smaller than the first diameter.

8. The medical instrument of claim 1, wherein the medical instrument is made from a material that includes stainless steel, and wherein the medical instrument is configured to be autoclaved between uses of the instrument.

9. The medical instrument of claim 1, wherein the medical instrument is made from a material that includes a polymer, and wherein the medical instrument is configured to be disposed of after a single use.

10. The medical instrument of claim 1, wherein each one of the plurality of extensions has a square shape.

11. A handheld medical instrument configured to double evert an eyelid of an animal, the instrument comprising:
    an elongated handle member, wherein the handle member includes a first end and a second end, wherein the handle member has an end-to-end length, and wherein the handle member has a longitudinal axis that contacts the handle member along an entirety of the end-to-end length of the handle member; and a plurality of extensions, including a first extension and a second extension, that extend from a top surface of the first end of the handle member at an angle that is substantially perpendicular to the longitudinal axis of the handle member, wherein the first extension is in a fixed position relative to the second extension, wherein the first extension is located on a first side of the top surface of the first end and the second extension is located on a second side of the top surface of the first end, wherein the first side is opposite the second side, wherein each one of the plurality of extensions has a handle end that couples to the top surface of the handle member and a distal end that is located at a distance away from the handle member, and wherein each one of the plurality of extensions has a paddle shape such that the first extension includes a rectangular neck at the handle end of the first extension and an oval-shaped segment coupled to the rectangular neck at the distal end of the first extension.

12. The medical instrument of claim 11, wherein the first extension and the second extension are both located at a first longitudinal position along the longitudinal axis of the handle member such that the first extension and the second extension are located directly across from one another on the top surface of the handle member.

13. The medical instrument of claim 11, wherein the first end of the handle member has a first diameter, and wherein the second end of the handle member is rounded and tapers from the first diameter to a second diameter that is smaller than the first diameter.

14. The medical instrument of claim 11, wherein the first end and the second end of the handle member have a first diameter.

15. A method for double everting an eyelid of an animal, the method comprising:
   providing a handheld medical instrument that includes:
      an elongated handle member, wherein the handle member includes a first end and a second end, and
      a plurality of extensions, including a first extension and a second extension, that extend from a top surface of the first end of the handle member at an angle that is substantially perpendicular to a longitudinal axis of the handle member, wherein the plurality of extensions are configured to grasp the eyelid, wherein the first extension is located on a first side of the top surface of the handle member and the second extension is located on a second side of the top surface of the handle member, and wherein the first side is opposite the second side;
   holding the eyelid to the second end of the handle member and rotating the medical instrument until the eyelid is placed in an everted position;
   moving the second end of the handle member away from the everted eyelid;
   positioning the plurality of extensions over a lower edge of the everted eyelid in order to grasp the everted eyelid with the plurality of extensions, wherein the positioning includes placing the first extension in front of the everted eyelid and placing the second extension behind the everted eyelid; and
   rotating the medical instrument until the grasped-everted eyelid is placed in a double-everted position.

16. The method of claim 15, wherein the everting of the eyelid by holding the eyelid to the second end of the handle member includes holding eyelashes of the eyelid to the second end of the handle member.

17. The method of claim 15, wherein the animal is a human, wherein the eyelid is coupled to an eye of the human, wherein a portion of the eye that is normally covered by the eyelid becomes exposed when the eyelid is placed in the double-everted position, and wherein the method further comprises:
   providing a slit lamp; and
   observing, using the slit lamp, the exposed portion of the eye.

18. The method of claim 15, wherein the moving of the second end of the handle member away from the everted eyelid includes holding the everted eyelid in the everted position in order to prevent the everted eyelid from returning to a non-everted position while moving the second end of the handle member.

19. The method of claim 15, wherein the animal is a human, wherein the eyelid is coupled to an eye of the human, wherein a portion of the eye that is normally covered by the eyelid becomes exposed when the eyelid is placed in the double-everted position, and wherein the method further comprises removing a foreign body from the exposed portion of the eye.

20. The method of claim 15, wherein the handheld medical instrument is made from a material that includes stainless steel, the method further comprising autoclaving the medical instrument between uses of the medical instrument.

* * * * *